United States Patent
Atlas et al.

(10) Patent No.: US 6,369,106 B1
(45) Date of Patent: *Apr. 9, 2002

(54) TREATMENT OF ISCHEMIC BRAIN INJURIES WITH BRAIN TARGETED ANTI OXIDANT COMPOUNDS

(75) Inventors: Daphne Atlas, Jerusalem; Eldad Melamed, Tel Aviv; Daniel Offen, Há Roe, all of (IL)

(73) Assignees: Yissum Research Development Company of the Hebrew University of Jerusalem, Jerusalem; Mor-Research Applications Ltd., Petach Tikua; Ramot University Authority for Applied Research & Industrial Development Ltd., Tel-Aviv, all of (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/472,033

(22) Filed: Dec. 27, 1999

Related U.S. Application Data

(63) Continuation-in-part of application No. 09/322,980, filed on Jun. 1, 1999, which is a continuation-in-part of application No. PCT/US97/23997, filed on Dec. 23, 1997, which is a continuation-in-part of application No. 08/773,153, filed on Dec. 26, 1996, now Pat. No. 5,874,468.

(51) Int. Cl.[7] ...................... A61K 31/225; A61K 31/22; A61K 31/195

(52) U.S. Cl. .......................... 514/547; 514/550; 514/562
(58) Field of Search ................................ 514/547, 550, 514/562; 560/147; 562/556

(56) References Cited

U.S. PATENT DOCUMENTS

| | | | |
|---|---|---|---|
| 5,736,565 A | | 4/1998 | Ferrari |
| 5,874,468 A | * | 2/1999 | Atlas et al. .................. 514/547 |
| 5,885,976 A | * | 3/1999 | Sandyk ........................ 519/159 |

OTHER PUBLICATIONS

CAPlUS AN 1995: 720776 to Heap et al., Biochem Pharmacol. vol. 50(2) pp. 263–270.

* cited by examiner

Primary Examiner—Marianne C. Seidel
Assistant Examiner—Donna Jagoe

(57) ABSTRACT

A method of reducing oxidative stress in the brain of an organism having a blood brain barrier and suffering an ischemic brain injury, the method comprising the step of administering a compound to the organism, the compound having (a) a combination of molecular weight and membrane miscibility properties for permitting the compound to cross the blood brain barrier of the organism; (b) a readily oxidizable chemical group for exerting antioxidation properties; and (c) a chemical make-up for permitting the compound or its intracellular derivative to accumulate within the cytoplasm of cells.

8 Claims, 6 Drawing Sheets

TREATMENT OF ISCHEMIC BRAIN INJURIES WITH BRAIN TARGETED ANTI OXIDANT COMPOUNDS

This is a continuation-in-part of U.S. patent application Ser. No. 09/322,980, filed Jun. 1, 1999, which is a continuation-in-part of PCT/US97/23997, filed Dec. 23, 1997, which is a continuation-in-part of U.S. patent application Ser. No. 08/773,153, filed Dec. 26, 1996, now U.S. Pat. No. 5,874,468, issued, Feb. 23, 1999.

FIELD AND BACKGROUND OF THE INVENTION

The present invention relates, in general to the use of antioxidant compounds, also referred herein as antioxidants, for the treatment of ischemic head injuries. More particularly, the present invention relates to novel brain targeted low molecular weight, hydrophobic antioxidants and their use in treatment of ischemic head injuries, such as, but not limited to stroke and head trauma.

Correlation Between Oxidative Stress and Various Neurodegenerative Pathologies

In the last few years evidences have accumulated which connect oxidative stress (OS) with the pathogenesis of Parkinson's, Alzheimer's Creutzfeldt-Jakob's diseases and other human neurodegenerative disorders (Olanow, 1990, 1993; Fahn and Cohen, 1992; Cafe et al., 1996, Brown et al., 1996; Thomas et al., 1996).

These studies were initiated (i) since outo-oxidation of levodopa and dopamine is known to produce oxygen free radicals, $H_2O_2$, quinones and semiquinones, the later two are high molecular weight polymers possessing an aromatic structure and are therefore potentially toxic and (ii) since post-mortem studies in Parkinson's disease patients showed a dramatic decline in the levels of endogenous reduced glutathione (GSH), which is, as is further delineated hereinbelow, essential for maintaining the oxidative state of the cells. The decrease in reduced glutathione levels progresses from the pre symptomatic Parkinson's disease condition to the advanced clinical Parkinson's disease condition.

Two possible explanations may account for the role played by oxidative stress in the pathogenesis of Parkinson's disease.

According to a first hypothesis it is assumed that cells of the substantia nigra (SN), are constantly under oxidative stress due to the oxidation of the catechol ring of dopamine. Dopamine, like other catecholamines, undergoes spontaneous oxidation to form semiquinones, oxygen free-radicals and $H_2O_2$ as metabolic by-products. In addition, one of the disposal routs for dopamine is its enzymatic oxidation by MAO (monamine oxidase) type A or B which, like the spontaneous oxidation, creates semiquinones, oxygen free radicals and $H_2O_2$.

These products may cause accumulative oxidation damage within the substantia nigra cells, and eventually lead to cell death. Non-affected cells increase the turnover of dopamine, which in turn, generates more toxic free radicals. Indeed, it was shown that in the presence of $H_2O_2$ and copper ions, dopamine as well as L-dopa (levodopa) cause oxidative damage to DNA (Jenner 1994; Spencer et al., 1994).

According to another hypothesis it is assumed that Parkinson's disease is caused by a substance of an unknown composition, similar to the toxin 1-methyl-4-phenyl-1,2,3, 6-tetrahydropyridine (MPTP), which is enzymatically converted to the toxic metabolite 1-methyl-4-phenyl pyridine ($MPP^+$) by MAO type B. Since this reaction releases free oxygen radicals, thereby increasing the oxidative stress imposed on the cells, similar mechanisms might affect the nigral cells in Parkinson's disease. If this type of a process indeed occurs in Parkinsonian brains, than again, it would create a high level of oxidative stress in the dopaminergic cells at the substantia nigra.

The following findings demonstrate a strong indication for oxidative stress as a possible cause for the pathogenesis of Parkinson's disease.

First, the iron content in the substantia Nigra of Parkinson's disease patients was found to be significantly higher while ferritin content, the protein which bind free iron ions within tissues, was found to be significantly lower then normal values (Olanow 1990; 1993 and Jenner 1994). These two phenomena indicate a situation where the amount of free iron which acts as a catalyst in oxidation reactions, is abnormally high and thus may contribute to the speed of oxidation reactions at the substantia nigra of Parkinson's disease patients. The above indication was given support when it was shown that injection of free iron directly into the substantia nigra of rodents caused the appearance of Parkinsonian symptoms, which symptoms could be overcome by addition of transferrin, the protein which binds free iron in the blood plasma (Jenner 1994).

Second, one of the protective mechanisms against oxidation processes in the brain is reduced glutathione (GSH), which upon oxidation to oxidized glutathione (GS), acts as a reducing agent. In the substantia nigra of Parkinson's disease patients the level of reduced glutathione is significantly low, whereas the level of oxidized glutathione remains normal. Hence the oxidation potential in the substantia nigra of Parkinson's disease patients is low. This change in the level of reduced glutathione is in all likelihood, specific for Parkinson's disease. The oxidation products which are formed during spontaneous and enzymatic oxidation of dopamine, as described hereinabove, lower the level of reduced glutathione, and thereby increase the ratio of oxidized/reduced glutathione. Since the level of γ-glutamyl-cysteine synthetase, the enzyme which is a rate limiting enzyme in the biochemical pathway of glutathione synthesis, is normal, the ratio stays high and induces a state of oxidative stress in the cells. It is interesting that the level of the enzyme which is responsible for the removal of oxidized glutathione, γ-glutamyl transpeptidase in the cells is higher, as if the cells attempt to overcome the increased oxidative stress by trying to get rid of oxidized glutathione (Sian et al., 1994).

Third, additional evidence for the abnormally high oxidative stress in the Parkinsonian brain comes from a study of lipid oxidation products in the substantia nigra of Parkinson's disease patients. In general, the level of unsaturated fatty acids is low in the substantia nigra, however, the level of lipid hydroperoxides which are the oxidation products of unsaturated fatty acids is high in the substantia nigra of Parkinson's patients. This finding indicates the presence of an abnormally higher frequency of oxidation processes in the Parkinsonian substantia nigra (Jenner, 1994).

And finally, one of the animal models which are currently used for the study of Parkinson's disease is created by the injection of 6-hydroxy-dopamine. Like dopamine, this false neurotransmitter elevates the level of the oxidation products during its degradation, thus leading to cell death. Since the biological half life of 6-hydroxy-dopamine is much longer and since it is readily taken-up by the cells, it increases the rate by which the animal develops the symptoms of the disease.

The different pathological makers of various neurodegenerative diseases e.g., Lewy bodies, plaques, etc., indicate different causal factors in the initiation of these diseases. However, there is growing evidence that once initiated, the progression of a large number of neurodegenerative diseases, is quite similar. Although the characteristic symptoms are descriptive for each neurodegenerative disease, it appears that elevation of the oxidative state of the cells at specific regions in the brain is an important factor in the etiology of Parkinson's disease, basal ganglia degenerative diseases, motoneuron diseases, Alzheimer's and also the Creutzfeldt-Jakob's disease.

An indication for a role played by oxidative stress in the pathogenesis of Alzheimer's disease was found while in a recent study, the relationship between the β-amyloid protein fragments and oxygen radical formation was tested in a system that is highly sensitive and responds to free oxygen radicals. This system utilizes the vasoactivity of the blood vessel which, in the presence of β-amyloid, enhances the phenylephrine mediated contraction of the vessels. Pre treatment of the blood vessel with superoxide dismutase (SOD), an enzyme that scavenges free oxygen radicals, eliminated the effect of β-amyloid, namely, there was no enhancement of vasoconstriction. Whereas, if SOD was added after treatment with β-amyloid protein, the protective effect of the radical scavenger was abolished (Thomas et al., 1996). Recently, other studies have shown that oxidative stress and free radicals production are linked to β-amyloid fragment which includes amino acids 25–35 and may contribute to neurodegenerative events associated with Alzheimer's disease (Cafe et al., 1996).

Possible indications for a role played by oxidative stress in the pathogenesis of Scrapie, spongyform encephalopathy (BSE) and Creutzfeldt-Jakob's diseases are listed hereinbelow.

In a recent study, it was demonstrated that the toxic effect of Scrapie requires the presence of microglia cells which respond to a prion protein fragment (PrP106-126) by increasing their oxygen radical production. Interestingly, all these effects were absolutely dependent on mice that express the prion protein PrPc (Brown et al., 1996). The contribution of progressive oxidative stress to the state of various diseases and to mechanism of cell death is further demonstrated in a study by P. Jenner in The Lancet (1994) 344, 796–798, which is incorporated by reference as if fully set forth herein.

New Therapeutic Aspects

The use of glial cell-derived neurotrophic factor (GDNF) was established as a potential stimulant for the increase of dopamine levels in midbrain of rhesus monkeys (Gash et al., 1996). This study which extends previous results obtained with rodents, is promising as a potential treatment for Parkinson's disease. However, like any other protein, GDNF cannot cross the blood brain barrier. Therefore, it can not be taken orally or be injected systemically. The only possible mode of administration would thus be via an intracerebral injection which would constitute a main drawback for such a treatment.

Similarly, in other neurodegenerative diseases such as Alzheimer's and Creutzfeldt-Jakob's, where the theory of free oxygen radicals appears to play a major role, there is no major breakthrough in therapy.

To overcome high oxidative stress it would be beneficial to augment the reduced state of the cells at the central nervous system (CNS). One of the possible ways to do it is by increasing the level of reduced glutathione or other scavengers of free radicals and free oxygen in the brain.

In general, in order to lower oxidative stress levels, various antioxidants are being used. The most common are vitamin E and vitamin C. However, vitamin E was found to be ineffective at decreasing the oxidative stress at the substantia nigra (The Parkinson Study Group, 1993, Offen et al., 1996) since this compound, although capable of crossing the blood brain barrier, is trapped in the cell membrane and therefore does not reach the cytoplasm where its antioxidant properties are needed. Vitamin C does not cross the blood brain barrier and therefore, cannot be used effectively for neurodegenerative diseases of central origin.

Recently, a similar approach for reducing the levels of free oxygen, was taken for the treatment of asthma (Bundy et al., 1995). A reactive oxygen inhibitor was synthesized (2,4-diaminopyrrolo-[2,3-d]pyrimidines) and after a successful pharmaceutical bio-availability and toxicity tests was selected for clinical evaluation.

A somewhat different approach involves stimulating the production of endogenous antioxidants, especially reduced glutathione. To this end a drug known as Procysteine which boosts cellular production of glutathione by loading the cells with cysteine is under clinical trials these days by Free Radical Sciences Inc. (CA, US) to treat conditions of acute respiratory distress syndrome (ARDS) which includes overproduction of oxidants or reactive oxygen species by the immune system. Other conditions in which overproduction of oxidants is experienced include but are not limited to amyotrophic lateral sclerosis, atherosclerotic cardiovascular disease and multiple organ dysfunction. See, for example, Charles Craig, 1996.

PCT/US97/23997 teaches novel brain targeted low molecular weight, hydrophobic antioxidants and the use of such antioxidants in treatment of central nervous system neurodegenerative disorders such as Parkinson's, Alzheimer's and Creutzfeldt-Jakob's diseases and in treatment of conditions of peripheral tissues such as acute respiratory distress syndrome, amyotrophic lateral sclerosis, atherosclerotic cardiovascular disease and multiple organ dysfunction, in which oxidants are overproduced. PCT/US97/23997, however, fails to teach the use of such antioxidants for treatment in cases of ischemic brain injuries.

Ischemic Brain Injury

Ischemic brain injury, due to, for example, stroke or head trauma, is a major cause of morbidity and mortality in adults but also of neurodevelopmental impairment and disability. The critical reduction of local cerebral blood flow and the resulting ischemia are associated with a catastrophic cascade of events that may affect and determine survival or death of neurons, the final territory of infracted tissue and the neurological outcome. Prominent among the biochemical features of ischemic injury is the loss of cellular ATP, resulting in increased intracellular $Na^+$ and $Ca^{2+}$, and decreased intracellular $K^+$. These ionic imbalances, together with a breakdown in cellular defense systems following ischemia, can contribute to enhanced local oxidative stress with a net increase in potentially harmful reactive oxygen species (ROS). Subsequent damage to lipids, proteins, DNA and inactivation of key cellular enzymes ultimately lead to cell death. Such damages occur after transient brain ischemia, and in the penumbral region of infarcts caused by permanent ischemia.

Although the precise mechanisms of neuronal loss are yet unclear, it is now clear that both apoptosis and necrosis are significant models of cell death following ischemia. Naturally, immediate re-establishment of arterial blood supply and oxygenation by clot lysis, e.g., using tissue plasminogen activator (tPA) can be helpful and positively affect for neurological prognosis. However, such an approach is impractical and may be too late for most patients with ischemic stroke. Therefore, it seems no less important to try and protect as many neurons as possible, particularly in the penumbra region. The suggested destructive mechanisms associated with ischemia are initiated by activation of glutamate receptors resulting in elevated intracellular $Ca^{2+}$ and ROS formation. Three major approaches have been investigated to counteract and prevent ischemia-induced brain damage: (i) interfering with the excitatory action of glutamate; (ii) preventing intracellular accumulation of $Ca^{2+}$; and (iii) preventing the destructive actions of reactive oxygen species (ROS). Interference with glutamate action can be achieved by: (i) facilitating mechanisms that maintain membrane potentials; (ii) blocking glutamate receptors; and (iii) inhibiting glutamate synthesis. Prevention of intracellular $Ca^{2+}$ accumulation may be achieved by: (i) blocking $Ca^{2+}$ channels; and (ii) facilitating endogenous $Ca^{2+}$ homeostatic mechanisms. Destructive actions of ROS can be minimized by: (i) administration of ROS-scavenging drugs; (ii) upregulating endogenous ROS-scavenging mechanisms; and (iii) preventing leukocyte invasion of the affected brain tissue.

Most, if not all, of the currently available antioxidants cannot penetrate the blood brain barrier (BBB) from the systemic circulation and therefore fail to decrease the ischemic damage in brains. Several studies have shown that raising the endogenous antioxidant defense can rescue neurons during ischemia. For instance, it was shown that transgenic mice overexpressing bcl-2 (an anti-apoptotic, anti-oxidant gene) in their neurons, are more resistant to induced ischemia (Martinou et al., 1994).

Furthermore, overexpression of thioredoxin, a redox-active disulfide/dithiol in transgenic mice, attenuates focal ischemic brain damage (Takagi et al., 1999).

These studies and others, strongly suggest that antioxidants that would effectively cross the BBB and penetrate into the ischemic tissue mainly at its penumbra, may help to maintain the redox status of the neurons, decrease ROS-associated neuronal damage. Thus reduce the neurological impairment and disability. If successful, the clinical, social and economical impact of the proposed novel strategy is enormous.

There is thus a widely recognized need for, and it would be highly advantageous to have a method for the use of antioxidants in treatment of ischemic brain injuries, because antioxidants that would effectively cross the BBB and penetrate into the ischemic tissue mainly at its penumbra, may help to maintain the redox status of the neurons and decrease ROS-associated neuronal damage, thus reduce the neurological impairment and disability.

SUMMARY OF THE INVENTION

According to one aspect of the present invention there is provided a method of reducing oxidative stress in the brain of an organism having a blood brain barrier and suffering an ischemic brain injury, the method comprising the step of administering a compound to the organism, the compound having (a) a combination of molecular weight and membrane miscibility properties for permitting the compound to cross the blood brain barrier of the organism; (b) a readily oxidizable chemical group for exerting antioxidation properties; and (c) a chemical make-up for permitting the compound or its intracellular derivative to accumulate within the cytoplasm of cells.

According to another aspect of the present invention there is provided a method of therapeutically or prophylactically treating an individual against ischemic brain injury, the method comprising the step of administering to the individual a pharmaceutical composition to the individual, the pharmaceutical composition including a pharmaceutically acceptable carrier and a therapeutically or prophylactically effective amount of an antioxidant compound, the antioxidant compound having (a) a combination of molecular weight and membrane miscibility properties for permitting the compound to cross the blood brain barrier of the individual; (b) a readily oxidizable chemical group for exerting antioxidation properties; and (c) a chemical make-up for permitting the compound or its intracellular derivative to accumulate within brain cells of the individual.

According to yet another aspect of the present invention there is provided a pharmaceutical composition for therapeutically or prophylactically treating an individual against ischemic brain injury, the composition comprising a pharmaceutically acceptable carrier and, as an active ingredient, a therapeutically or prophylactically effective amount of an antioxidant compound, the compound having (a) a combination of molecular weight and membrane miscibility properties for permitting the compound to cross the blood brain barrier of the individual; (b) a readily oxidizable chemical group for exerting antioxidation properties; and (c) a chemical make-up for permitting the compound or its intracellular derivative to accumulate within brain cells of the individual.

According to further features in preferred embodiments of the invention described below, the compound is selected from the group consisting of N-acetyl cysteine ethyl ester (compound A), β,β-dimethyl cysteine ethyl ester (compound B), N-acetyl-β,β-dimethyl cysteine (compound C), Glutathione ethyl ester (compound D), N-acetyl glutathione ethyl ester (compound E), N-acetyl glutathione (compound F), N-acetyl α-glutamyl ethyl ester cysteinyl glycyl ethyl ester (compound G) N-acetyl α-glutamyl ethyl ester cysteinyl glycyl (compound H), N-acetyl glutathione amide (compound I), N-acetyl cysteine amide (compound J), N-acetyl β,β dimethyl cysteine amide (compound K) and N-acetyl cysteine glycine amide.

According to still further features in the described preferred embodiments the ischemic brain injury is a result of a stroke or a head trauma.

According to still further features in the described preferred embodiments the pharmaceutically acceptable carrier is selected from the group consisting of a thickener, a carrier, a buffer, a diluent, a surface active agent and a preservatives.

According to still further features in the described preferred embodiments the administration is peripheral.

According to still further features in the described preferred embodiments the peripheral administration is selected from the group consisting of topical administration, oral administration, administration by inhalation, and parenteral administration.

According to still further features in the described preferred embodiments the readily oxidizable chemical group is a sulfhydril group.

According to still further features in the described preferred embodiments the chemical make-up is selected having an ester moiety which is removable by hydrolysis imposed by intracellular esterases.

According to still further features in the described preferred embodiments the administration is peripheral.

According to still further features in the described preferred embodiments the ester moiety is selected from the group consisting of alkyl ester and aryl ester.

According to still further features in the described preferred embodiments the alkyl and aryl esters are selected from the group consisting of methyl ester, ethyl ester, hydroxyethyl ester, t-butyl ester, cholesteryl ester, isopropyl ester and glyceryl ester.

According to still further features in the described preferred embodiments the organism is a human being.

The present invention successfully addresses the shortcomings of the presently known configurations by providing a novel method and pharmaceutical composition for the therapeutic or prophylactic treatment of ischemic brain injuries, such as stroke and head trauma.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
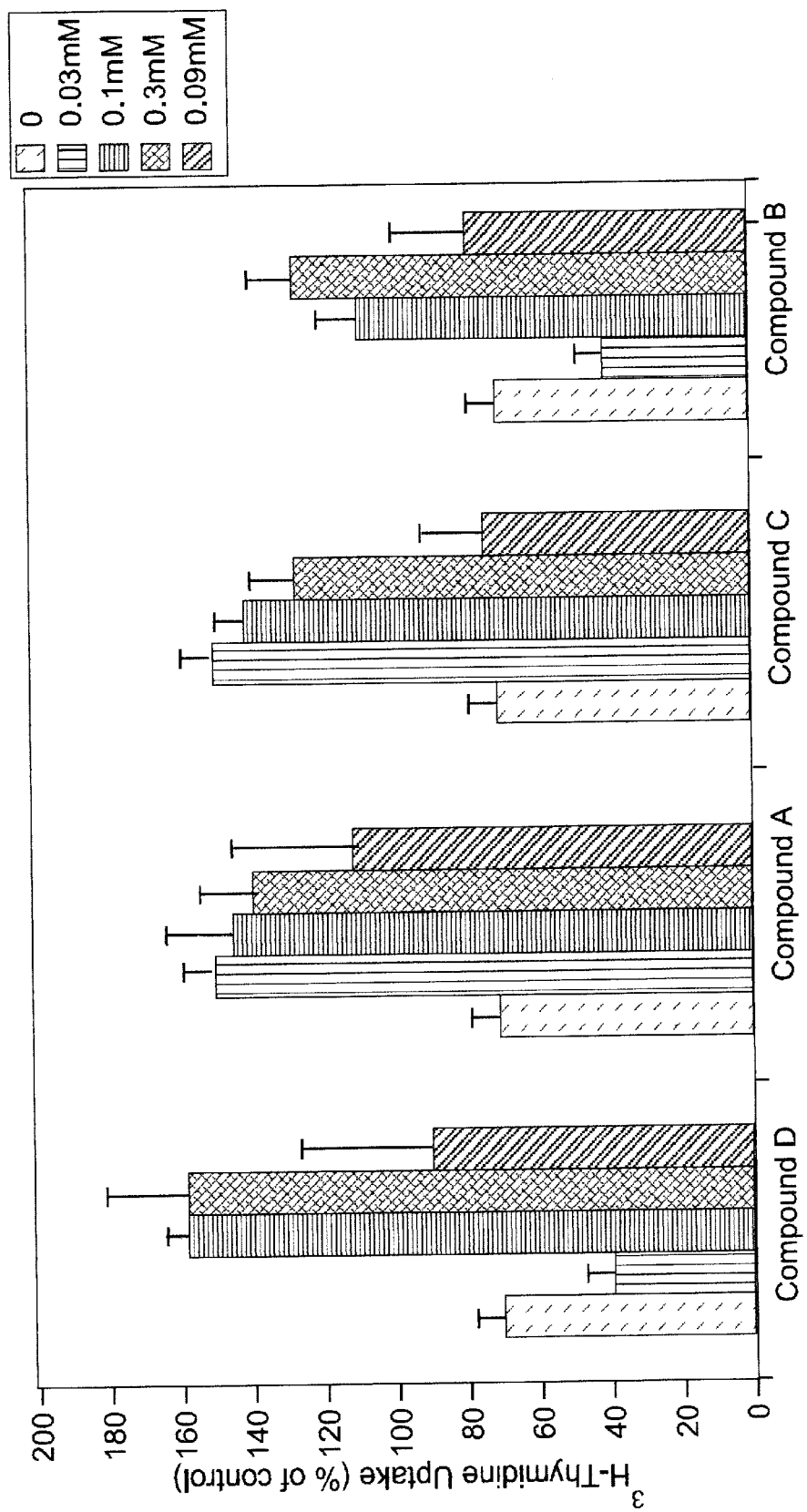
FIG. 1 presents [$^3$H]-thymidine uptake by PC12 cells treated in vitro with 0.5 mM dopamine which confers extracellular oxidative stress by forming oxidation products during its oxidation in the medium rescued with various concentrations of compounds A–D.

The present invention is of composition and use of antioxidant compounds. Specifically, the compounds of the present invention are low molecular weight, hydrophobic antioxidants which can be used for treatment of ischemic brain injuries, such as stroke and head trauma.

The principles of operation of the compounds according to the present invention may be better understood with reference to the drawings and accompanying descriptions.

Before explaining at least one embodiment of the invention in detail, it is to be understood that the invention is not limited in its application to the details set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Antioxidant compounds are used according to the present invention to relieve oxidation stress within cells of a brain suffering Ischemic brain injury according to the present invention may be due to short in oxygen supply to the brain, due to, for example, (i) short in blood supply to the brain, in cases of, for example, heart failure, delivery complications (fetus brain), massive blood loss, etc.; (ii) short in blood oxygenation, due to, for example, short in atmosphere oxygen supply, CO poisoning, suffocation, lung failure/obstruction, etc.; and (iii) hemorrhage in the brain or a region thereof, due to, for example, stroke or head trauma.

Preferred compounds which are used to relieve oxidation stress according to the present invention (i) has a combination of molecular weight and membrane miscibility properties rendering it capable of crossing the blood brain barrier; (ii) includes a readily oxidizable (i.e., reduced) chemical group, such as, but not limited to, a sulfhydryl (—SH) group, for exerting its antioxidation properties and (iii) has a chemical make-up for permitting it or its cellular derivative (s) to accumulate within the cytoplasm of cells, such as brain cells. Collectively, these properties render the compounds suitable for treatment of head injuries.

Compounds which have the above listed properties are for example:

(i) N-acetyl cysteine ethyl ester —$C_7H_{11}NO_3S$— of a formula (compound A):

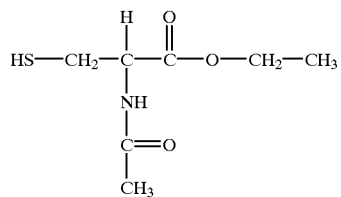

(ii) β,β-dimethyl cysteine ethyl ester or N-acetyl-penicillamine ethyl ester —$C_9H_{18}NO_3S$— of a formula (compound B):

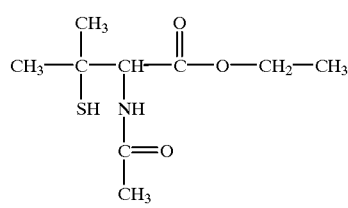

(iii) N-acetyl-β,β-dimethyl cysteine or N-acetyl-penicillamine —$C_7H_{13}NO_3S$— of a formula (compound C):

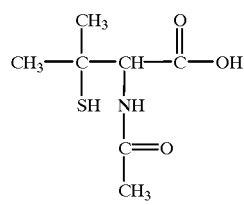

(iv) Glutathione ethyl ester —$C_{12}H_{21}N_3O_6S$— of a formula (compound D):

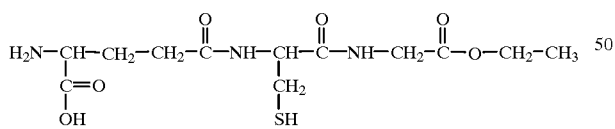

(v) N-acetyl glutathione ethyl ester —$C_{14}H_{23}N_3O_7S$— of a formula (compound E):

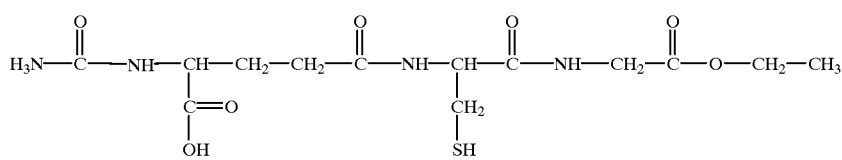

(vi) N-acetyl glutathione —$C_{12}H_{19}N_3O_7S$— of a formula (compound F):

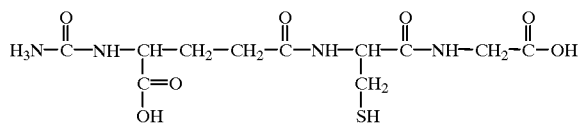

(vii) N-acetyl α-glutamyl ethyl ester cysteinyl glycyl ethyl ester or N-acetyl (α-ethyl ester) glutathione ethyl ester —$C_{16}H_{27}N_3O_7S$— of a formula (compound G):

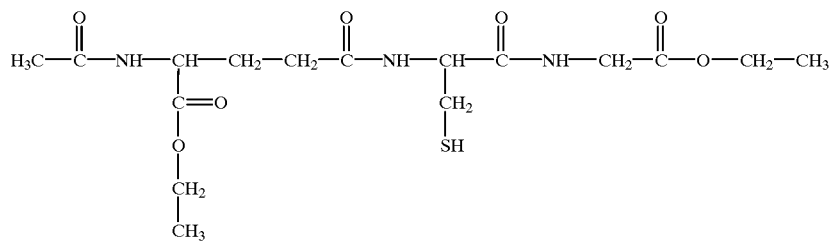

(viii) N-acetyl α-glutamyl ethyl ester cysteinyl glycyl or N-acetyl (α-ethyl ester) glutathione —$C_{14}H_{23}N_3O_7S$— of a formula (compound H):

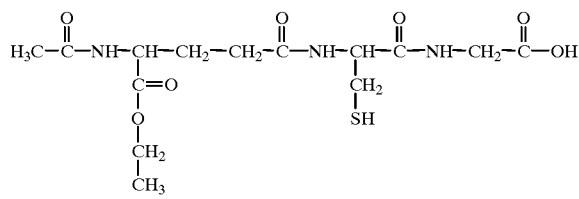

Additional compounds which may serve as antioxidants according to the present invention are:

(ix) N-acetyl glutathione amide —$C_{12}H_{21}N_5O_5S$— of a formula (compound I):

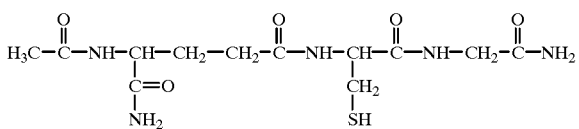

(x) N-acetyl cysteine amide —$C_5H_{10}N_2O_2S$— of a formula (compound J):

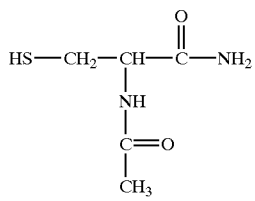

(xi) N-acetyl β,β dimethyl cysteine amide —$C_7H_{15}N_2O_2S$— of a formula (compound K):

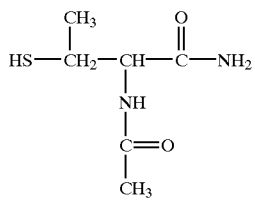

(xii) N-acetyl cysteine glycine amide —$C_7H_{12}N_3O_3S$— of a formula (compound L):

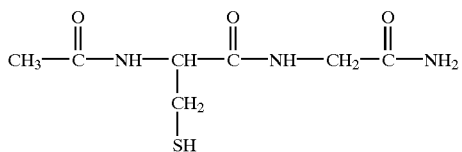

These compounds are used according to the invention as antioxidants which cross the blood brain barrier, for relieving oxidative stress in case of ischemic brain injury, such as stroke and head trauma.

According to a preferred embodiment of the invention, the compound is a pro-drug which penetrates the cells due to its solubility in the cell membrane and is hydrolyzed once inside the cell, exerting a drug having the antioxidant activity. For example compounds A, B, D, E, G and H above are pro-drug compounds.

Compounds A, B, E, G and H above are novel pro-drug compounds, and their hydrolytic products ethanol and N-acetyl-cysteine (for compound A); ethanol and N-acetyl-penicillamine (for compound B); ethanol and N-acetyl glutathione (for compounds E, G and H) are known not to be toxic. The lethal dose 50% (LD50) value for N-acetyl-cysteine is 5,050 mg/kg. N-acetyl-penicillamine is available as an oral medication distributed under the generic name cuprimine by various manufacturers. Whereas N-acetyl glutathione and ethanol are both well known to be non-toxic substances.

A pro-drug according to the invention includes at least one ester moiety such as an alkyl ester or an aryl ester, e.g., methyl ester, ethyl ester, hydroxyethyl ester, t-butyl ester, cholesteryl ester, isopropyl ester and glyceryl ester. Preferably the pro-drug includes an ethyl ester moiety which, on one hand, neutralizes the charge of the carboxylic group(s) and on the other hand, when hydrolyzed within the cells release ethanol which is a substance known not to be toxic to the cells.

Upon entering the cytoplasm of a cell, the pro-drug is de-esterified by one or various intracellular esterases, to release the drug which has at least one carboxyl moiety (—COOH) and a by-product (typically ethanol) which contains the hydroxyl moiety (—OH). The carboxylic group(s) of the drug is typically negatively charged and the drug therefore is trapped within the cell, where it is to exert its antioxidative properties.

Compounds A and B are synthesized as follows. First, N-acetyl cysteine (for compound A) or N-acetyl β,β-dimethyl cysteine (for compound B) is mixed with a cooled solution of thionyl chloride and absolute ethanol. Second, the mixture is refluxed. And third, the volatiles are removed from the mixture for obtaining a first residue. Preferably the method further includes the following step. Fourth, the first residue is dissolved in water. And fifth, the first residue is extracted from the water with methylene chloride. Preferably the method further includes the following step. Sixth, the extract is dried to obtain a second residue. Preferably the method further includes the following step. Seventh, the second residue is crystallized from petroleum ether (for compound A) or from a methanol water solution (for compound B). Further detail concerning the method of preparing compounds A and B are delineated hereinbelow in the Examples section.

Compound C is described in Biochem. Prep. 3, 111 (1953) and in U.S. Pat. Nos. 2,477,148 and 2,496,426, both are incorporated by reference as if fully set forth herein, and was prepared essentially as therein described. As mentioned above, compound C, N-acetyl-penicillamine, is available as an oral medication distributed under the generic name cuprimine by various manufacturers.

Compound D above is commercially available from Sigma Biochemicals, Cat. No. G1404. Compounds D is a pro-drug compound, and its hydrolytic products ethanol and glutathione are well known not to be toxic.

Compounds E, G and H above are novel glutathione derivatives and can be prepared, for example, from commercially available building units for Boc and Fmoc chemistry peptide synthesis, as well known in the art.

Compound F is a glutathione derivative and is described in Levy et al., 1993.

Compounds I, J and K are synthesized as follows. First, ammonia gas is bubbled through absolute cooled dry ethanol. Second, N-acetyl glutathione ethyl ester (compound G, for synthesis of compound I), N-acetyl cysteine ethyl ester (compound A, for synthesis of compound j) or N-acetyl , dimethyl cysteine ethyl ester (compound B, for synthesis of compound K) is added to the ethanol solution. Third, a container holding the reaction is sealed. Fourth, access ammonia and ethanol are evaporated and finally the resulting product is lyophilized. Further detail concerning the method of preparing compounds I, J and K are delineated hereinbelow in the Examples section.

The synthesis of Compound L is further detailed in the Examples section that follows.

Any of the glutathione derived compounds (D–H and I) according to the invention may be prepared employing Boc and Fmoc chemistry for peptide synthesis. This, in turn, permits the inclusion of native Levo (L isomer) and/or non-native Dextro (D isomer) glutamic acid and/or cysteine derivatives or residues within any of these compounds. It will be appreciated that by replacing the native L configuration by the non-native D configuration, a compound becomes less recognizable by many enzymes and its biological half life within the body therefore increases. Compounds A–C and J–K also include chiral carbons. Any of these carbons may also acquire a D or an L isomeric configuration.

Thus, compounds A–L above were given chemical names according to all L isomer configurations, i.e., all of their chiral carbon atoms are L isomers. However, as used herein in the specification and in the claims, these chemical names also refer to any of their D isomer(s) containing chiral atoms.

As mentioned above, compounds D–H are glutathione derivatives. These compounds and similar glutathione derivative compounds are represented by the general formula:

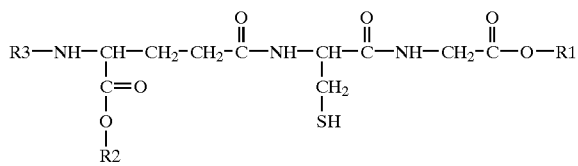

R1 is selected from the group consisting of a hydrogen atom and an alkyl (e.g., $C_1$–$C_{20}$) or aryl (e.g., $C_6$–$C_9$) group. Preferably R1 is an ethyl group.

R2 is selected from the group consisting of a hydrogen atom and an alkyl (e.g., $C_1$–$C_{20}$) or aryl (e.g., $C_6$–$C_9$) group. Preferably R2 is a ethyl group.

Whereas, R3 is selected from the group consisting of a hydrogen atom and an R4-CO (acyl) group, wherein R4 is an alkyl (e.g., $C_1$–$C_{20}$) or aryl (e.g., $C_6$–$C_9$) group. Preferably R4 is a methyl group. However, any one of R1, R2 and R4 can independently be a methyl, ethyl, hydroxyethyl, t-butyl, cholesteryl, isopropyl or glyceryl group.

Compounds A, B and E–L are not listed in the Chemical Abstract.

For therapeutic or prophylactic treatment of ischemic brain injuries, the antioxidant compounds of the present invention can be formulated in a pharmaceutical composition, which may include thickeners, carriers, buffers, diluents, surface active agents, preservatives, and the like, all as well known in the art. Pharmaceutical compositions may also include one or more additional active ingredients, such as, but not limited to, antiinflammatory agents, antimicrobial agents, anesthetics and the like in addition to the antioxidant compounds.

The pharmaceutical composition of the present invention may be administered in either one or more of ways depending on whether local or systemic treatment is of choice, and on the area to be treated.

Administration may be done topically (including ophthalmically, vaginally, rectally, intranasally), orally, by inhalation, or parenterally, for example by intravenous drip or intraperitoneal, subcutaneous, intramuscular or intravenous injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates. Administration is preferably effected as soon as a stroke or head trauma are diagnosed, or prophylactically prior to medical treatments which may cause blood clotting which may lead to stroke.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference in now made to the following examples, which together with the above descriptions, illustrate the invention.

Example 1

Synthesis of N-acetyl Cysteine Ethyl Ester (Compound A)

N-acetyl cysteine (4.6 mmol) was added in portions to a cooled (e.g., 2–8° C.) solution of 2 ml thionyl chloride and 10 ml absolute ethanol. The resulting mixture was refluxed at 40° C. for 1 hour and then the volatiles were removed in vacuo. The residue was dissolved in 10 ml of water and was extracted twice with 20 ml of methylene chloride. The extract was dried under vacuo. The title compound was crystallized from petroleum ether (fraction 40–60°) in 55% yield.

The resulting product has the following characteristics:
(a) Melting point of 90° C.
(b) Anal. calculated for $C_7H_{11}NO_3S$:

| Calculated: | C, 43.9 | H, 6.8 |
| Found: | C, 42.5 | H, 6.0 |

(c) Thin layer chromatography in n-butanol/acetic acid/water (4/1/4) was carried out and the Rf value was Rf=0.91. The Rf value of the reactant, N-acetyl cysteine is 0.78.

(d) Nuclear Magnetic Resonance (NMR) in deutarated trichloromethane (CDCl3):
6.51, 0.7H
4.85, 1H, m
4.23, 2H, q, J=7.0
3.44, 0.4H, d, J=4.4
3.22, 2H, t, J=4.4
2.06, 3H, S
1.30, 3H, t, J=7.0

Example 2

Synthesis of N-acetyl β,β-dimethyl Cysteine Ethyl Ester or N-acetyl-penicillamine Ethyl Ester (Compound B)

N-acetyl β,β-dimethyl cysteine (2.6 mmol) was added in portions to a cooled (2–8° C.) solution of 2 ml thionyl chloride and 10 ml absolute ethanol. The resulting mixture was refluxed at 40° C. for 1 hour and then the volatiles were removed in vacuo. The residue was dissolved in 10 ml of water and was extracted twice with 20 ml of methylene chloride. The extract was dried under vacuo. The title compound was crystallized from a methanol-water solution (1/100, fraction 40–60°) in 25% yield.

The resulting product has the following characteristics:
(a) Melting point of 180° C.
(b) Thin layer chromatography in n-butanol/acetic acid/water (4/1/4) was carried out and the Rf value was Rf=0.66. The value of the reactant, N-acetyl β,β-dimethyl cysteine is 0.88.
(c) Nuclear Magnetic Resonance (NMR) in deuterated acetone ($D_6$)
4.79, 1H, d, J=6.0
4.17, 2H, q, J=7.0
2.81,1H, d, J=6.0
1.98, 3H, S
1.44, 6H, S
1.27, 3H

Example 3

Synthesis of N-acetyl Glutathione Amide (Compound I)

Ammonia gas was bubbled through absolute dry ethanol at −70° C. (dry ice with acetone), for 10 minutes. N-acetyl glutathione ethyl ester (compound G), 350 mg (1 mmol) was added to the cooled ethanol/ammonia solution and ammonia was continued to bubble through the solution for additional 10 minutes. Then, the solution was corked and was left at room temperature. After 16 hours, the flask was opened and access of ammonia and the ethanol were evaporated under reduced pressure. The product was lyophilized. The yield was 84%.

The resulting product has the following characteristics:
(a) Thin layer chromatography in n-butanol/acetic acid/water (4/1/4) was carried out and the Rf value was Rf=0.71.

Example 4

Synthesis of N-acetyl Cysteine Amide (Compound J)

Ammonia gas was bubbled through absolute dry ethanol at −70° C. (dry ice with acetone), for 10 minutes. N-acetyl cysteine ethyl ester (compound A), 163 mg (1 mmol) was added to the cooled ethanol/ammonia solution and ammonia was continued to bubble through the solution for additional 10 minutes. Then, the solution was corked and was left at room temperature. After 16 hours, the flask was opened and access of ammonia and the ethanol were evaporated under reduced pressure. The product was lyophilized. The yield was 98%.

The resulting product has the following characteristics:
(a) Thin layer chromatography in n-butanol/acetic acid/water (4/1/4) was carried out and the Rf value was Rf=0.70.

The Rf value of the reactant, N-acetyl cysteine ethyl ester is 0.91.

Alternatively, a solution of 20% piperidine (4 ml) in 16 ml DMF was added to Fmoc Rink amide AM resin (2 gram; 1.1 mmole amide) and the reaction was allowed to proceed for 30 minutes. Ac-S-trityl cysteine (1.3 gram, 3.3 mmole) was added with TBTU (1.06 gram) followed by diisopropyl ethyl amine (1.12 ml). The reaction was carried out for 2 hours. The resin was washed with methylene chloride (×6), and then a mixture of 1 ml silan/0.5 ml water/19 ml of TFA was added. After 1 hour the resin was filtered washed with TFA and solvents evaporated. The product was dissolved in water and extracted with methylene chloride. The aqueous solution was thereafter lyophyllized.

The resulting product has the following characteristics:
(a) Nuclear Magnetic Resonance (NMR)
4.45 t,1,j=6.96 Hz
2.81 ABX system, $J_{AB}$=12.69, $J_{AX}$+$J_{BX}$=12.45 Hz
2.00 s 3 Hz

Example 5

Synthesis of N-acetyl β,β Dimethyl Cysteine Amide (Compound K)

Ammonia gas was bubbled through absolute dry ethanol at −70° C. (dry ice with acetone), for 10 minutes. N-acetyl β,β dimethyl cysteine ethyl ester (compound B), 194 mg (1 mmol) was added to the cooled ethanol/ammonia solution and ammonia was continued to bubble through the solution for additional 10 minutes. Then, the solution was corked and was left at room temperature. After 16 hours, the flask was opened and access of ammonia and the ethanol were evaporated under reduced pressure. The product was lyophilized. The yield was 90%.

The resulting product has the following characteristics:
(a) Thin layer chromatography in n-butanol/acetic acid/water (4/1/4) was carried out and the Rf value was Rf=0.50. The Rf value of the reactant, N-acetyl β,β dimethyl cysteine ethyl ester is 0.66.

Example 6

Synthesis of N-acetyl Cysteine Glycine Amide (Compound L)

A solution of 20% piperidine (4 ml) in 16 ml DMF was added to Fmoc Rink glycine amide AM resin (1.1 mmole amide) and the reaction was allowed to proceed for 30 minutes. Ac-S-trityl cysteine (1.3 gram, 3.3 mmole) was then added with TBTU (1.06 gram) followed by diisopropyl ethyl amine (1.12 ml). The reaction was carried out for 2 hours. The resin was washed with methylene chloride (×6), and then a mixture of 1 ml silan/0.5 ml water/19 ml TFA was added. After 1 hour the resin was filtered washed with TFA and solvents were evaporated. The product was dissolved in water and extracted with methylene chloride. The aqueous solution was lyophilized.

Example 7

In vitro Extracellular Antioxidation by Compounds A–D

Compounds A–D were assayed in vitro for their extracellular antioxidant activities. The assays were carried out with PC12 cells (Offen et al., 1996) subjected to a high dose of dopamine which confers oxidative stress to these cells by forming oxidation products during its oxidation in the growth medium, i.e., extracellularly.

With reference now to FIG. 1. To this end, PC12 cells were subjected to high concentration of dopamine (0.5 mM) for 24 hours in the presence of increasing concentrations (0 mM, 0.03 mM, 0.1 mM, 0.3 mM and 0.9 mM) of the various compounds A–D. [$^3$H]-thymidine was added to the cells (1 μCi/100,000 cells) six hours before the end of the 24 hours period. Due to the high lipophylicity of compounds A–D, the compounds were first dissolved in dimethyl sulfoxide (DMSO) and then in water and were applied to the cells in a final concentration of 3% DMSO. The effect of 3% DMSO on the cells was tested separately and the values presented in FIG. 1 are after the appropriate corrections.

[$^3$H]-thymidine uptake was measured in triplicate wells containing cells pretreated with dopamine alone and dopamine with each of compounds A–D at the concentrations as indicated above. The results presented in FIG. 1 show the mean of triplicate wells taken from three independent cell batches, wherein control represent cells treated only with 3% DMSO and is defined as 100% [$^3$H]-thymidine uptake (not shown).

Please note that all compounds A–D increased [$^3$H]-thymidine uptake at least at one concentration value. Increase varied between Ca. 1.5 (compound B at 0.03 mM) to Ca. 2.5 (compound D at 0.03 mM and 0.1 mM). Thus, all four compounds showed high potency as protective extracellular antioxidants. Furthermore, some also reversed the basal cellular oxidation state which occurs spontaneously in control cells (not shown). Thus compounds A–D were proven useful as extracellular antioxidants.

Example 8

In vitro Intracellular Antioxidation by Compounds A–D

One of the main characteristics of the oxidative effects in PC12 cells are mimicked by 6-hydroxy-dopamine which is a false neurotransmitter taken up by the cells. Therefore, 6-hydroxy-dopamine was used as another oxidative agent and tested the protective antioxidant efficiencies of compounds A–D within the cells.

Figure 2:
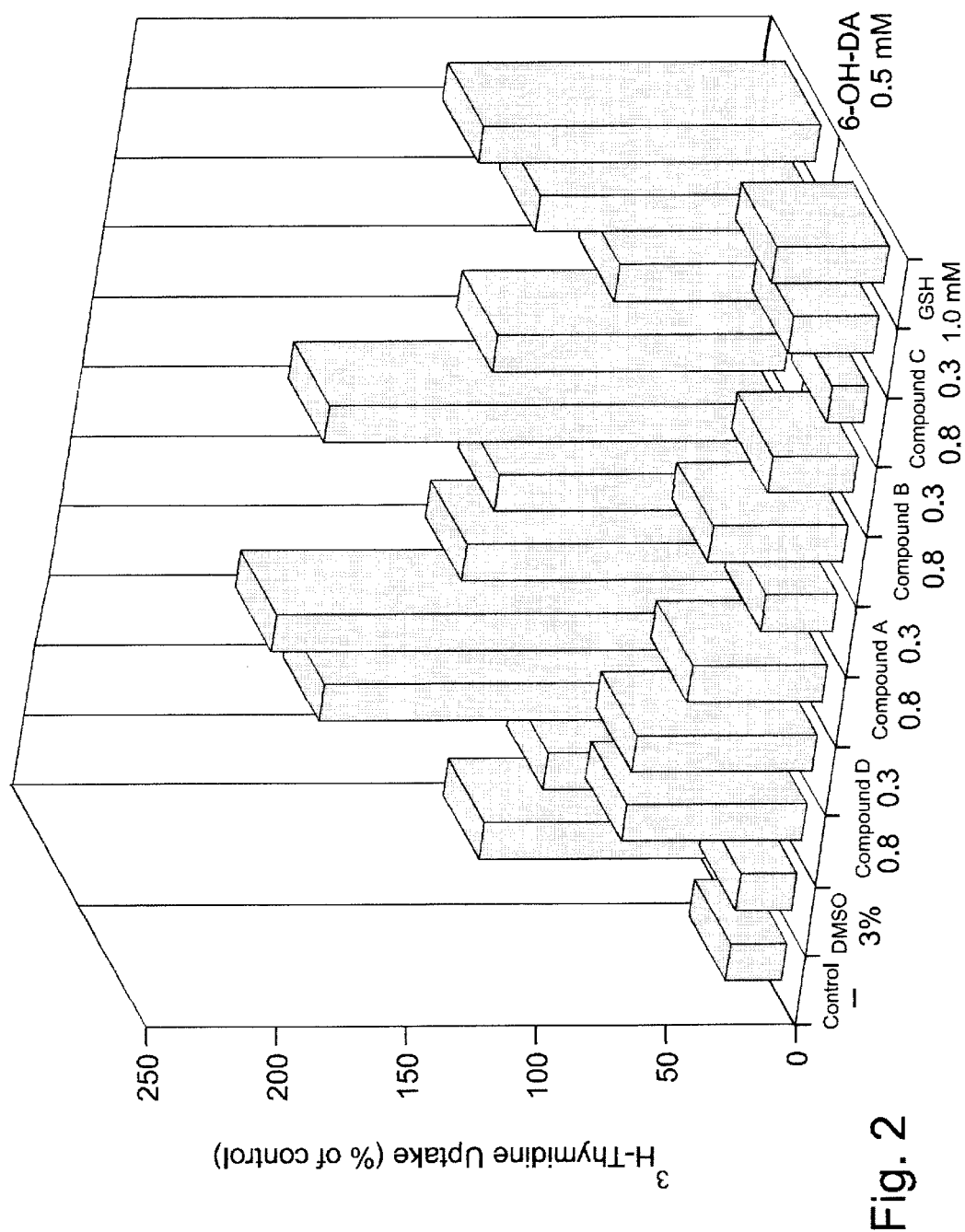
FIG. 2 presents [$^3$H]-thymidine uptake by PC12 cells treated in vitro with 0.5 mM 6-hydroxy-dopamine, which confers intracellular oxidative stress by first entering the cytoplasm and then forming oxidation products during its oxidation in the cytoplasm, protected with various concentrations of compounds A–D and exogenous reduced glutathione (GSH)

With reference now to FIG. 2. To this end, PC12 cells were subjected to high concentration (0.5 mM) of 6-hydroxy-dopamine (6-HO-DA) for 24 hour, in the presence of 0.3 mM or 0.8 mM of compounds A–D or 1 mM of reduced glutathione (GSH) a natural antioxidant, as shown in the front row of FIG. 2. A similar set of cells was treated with the same concentrations of compounds A–D and of reduced glutathione, yet without 6-hydroxy-dopamine, as shown in the back row of FIG. 2. Due to the high lipophylicity of the antioxidants used, they were first dissolved in dimethyl sulfoxide (DMSO), then in water and were applied to the cells in a final concentration of 3% DMSO. [$^3$H]-thymidine was added to the cells (1 $\mu$Ci/100,000 cells) six hours prior to the end of the 24 hour period.

The results presented in FIG. 2 are the mean of triplicate wells taken from three independent cell batches wherein control represent un-treated cells and is defined as 100% [$^3$H]-thymidine uptake. The effect of DMSO on the cells was tested separately as shown.

Please note that all compounds A–D increased [$^3$H]-thymidine uptake of 6-hydroxy-dopamine treated cells, at least at one concentration value. Increase varied between Ca. 1.5 (compound C at 0.3 mM) to Ca. 3.5 (compound D at 0.3 mM and 0.8 mM). Thus, all four compounds showed high potency as protective intracellular antioxidants. Furthermore, some also reversed the basal cellular oxidation state which occurs spontaneously in cells not treated with 6-hydroxy-dopamine (FIG. 1, back row). Thus compounds A–D were proven useful as intracellular antioxidants.

Example 9

In vivo Antioxidation by Compounds A–D

To demonstrate that indeed compounds A–D cross the blood brain barrier and affect oxidation state of brain cells, animals were injected with compound A and the endogenous reduced glutathione (GSH) amounts in the serum, in the corpus striatum (at the central nervous system) and/or in the whole brain were determined to evaluate compound A's antioxidation activity within the brain, as was determined by the ratio between endogenous brain (corpus striatum) GSH and endogenous serum GSH.

Figure 3:
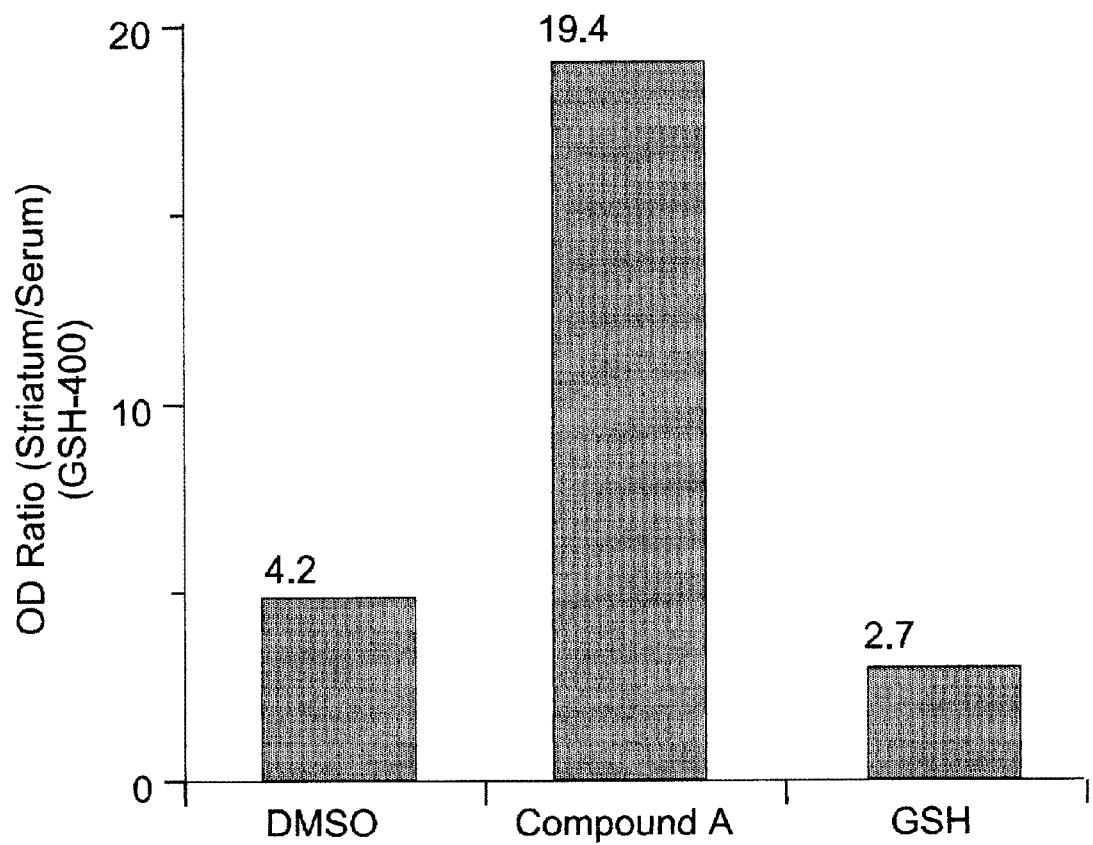
FIG. 3 presents the ratio of endogenous reduced glutathione levels in striatum/serum in two mice injected with 100 mg/kg of compound A in 3% DMSO, 100 mg/kg of reduced glutathione in 3% DMSO, and 3% DMSO injected as a control group, wherein the ratio obtained is marked at the top of the columns. The results represent two animals where each striatum taken separately.

With reference now to FIG. 3. To this end, three groups of two months old Balb/c mice containing two animals in each group were injected intraperitonealy (IP) with 100–300 mg/kg body weight of compound A. Blood samples were drawn from the tail three hours post injection and then the animals were sacrificed and either the corpus striatum or the whole brain were removed and analyzed for GSH levels.

GSH levels were determined using the experimental procedures as described hereinbelow and/or the GSH-400 kit (Oxis International, Inc.).

Preparation of brain homogenates: Animals were rapidly killed and exsanguinated to remove excess blood from the brain. The brain of each animal was rinsed in a beaker containing water, lightly blotted to dry and were weighted. The striatums were transferred into a hand-homogenizer tube and each was homogenized using a constant number (e.g., 20) of up and down strokes of the hand-homogenizer pestle. Each of the homogenates was poured into a centrifuge tube and centrifuged for 10,000×g for 5 min. The supernatant was used for GSH determination as follows.

GSH Assay: For each measurement, 200 $\mu$l of sample were incubated with 20 $\mu$l DTNB [5,5' dithio bis(2-nitrobenzoic acid)] for 1 hour in 37° C. Final absorbance was measured at 400 nm. Similar results were obtained using the GSH-400 kit.

The results shown in FIG. 3 are presented as the OD ratio of striatum/serum endogenous GSH levels. Two control mice were injected with dimethylsulfoxide (DMSO), since DMSO was used as vehicle for the injection of compound A. Exogenous GSH was also administered and used as a control for an antioxidant known not to cross the blood brain barrier.

These results demonstrate that compound A injected IP crosses the blood brain barrier and upon entry to cells at the striatum, increases the level of endogenous GSH, demonstrating its potential protection against oxidative stress.

Example 10

In vivo Antioxidation by Compound J

Detection of compound j (referred to in this Example also as CEA) was established using high performance liquid chromatography (HPLC). To this end, CEA was treated with a fluorescent thiolyte reagent (monobromobimane reagent) and analyzed on an HPLC column.

Protection from oxidative stress in vitro: Neuroblastoma SHSY5Y (NB) cells were maintained in Dulbeco's Modified Eagle's Medium (DMEM), supplemented with 8% FCS and 8% horse serum, penicillin (25 $\mu$g/ml), streptomycin (25 $\mu$g/ml), 2 mM L-glutamine and 400 $\mu$g/ml G418 (Gibco/BRL). For protection experiments cells were subcultured (in 2% serum) to poly-L-lysine-coated 96-well microtiter plates (Nunc), 100 $\mu$l of 5×10$^5$ cells/ml, CEA was applied to the cells in each well and 4 hours later DA, L-dopa (levodopa), 6-OHDA and MPP+ were added for 24 hours.

Survival was assayed by adding neutral red (0.34%, Sigma) to cells in DCCM-1 medium (0.1 ml/well, Bet-Haemek) and incubation for 2 hour at 37° C. The cells were then washed with cold PBS containing 10 mM MgCl$_2$ and the dye was dissolved in 50% ethanol in 50% Somerson buffer (70 mM sodium citrate, 30 mM citric acid, 0.1 N HCl). ELISA reader (590 nm) was used to measure the remaining color intensity.

Crossing the blood-brain-barrier: In vivo experiments were carried out on C57BL/6J mice (15 grams) injected IP with compound J. After incubation (15 min, 60 min or 4 hours) the mice were anesthetized with ether and blood samples were drawn. Then mice underwent perfusion with 50 ml of saline, injected into the right ventricle. The levels of compound I in the brain and in the plasma were detected by selective fluorescent labeling using high performance liquid chromatography (HPLC).

Figure 4:
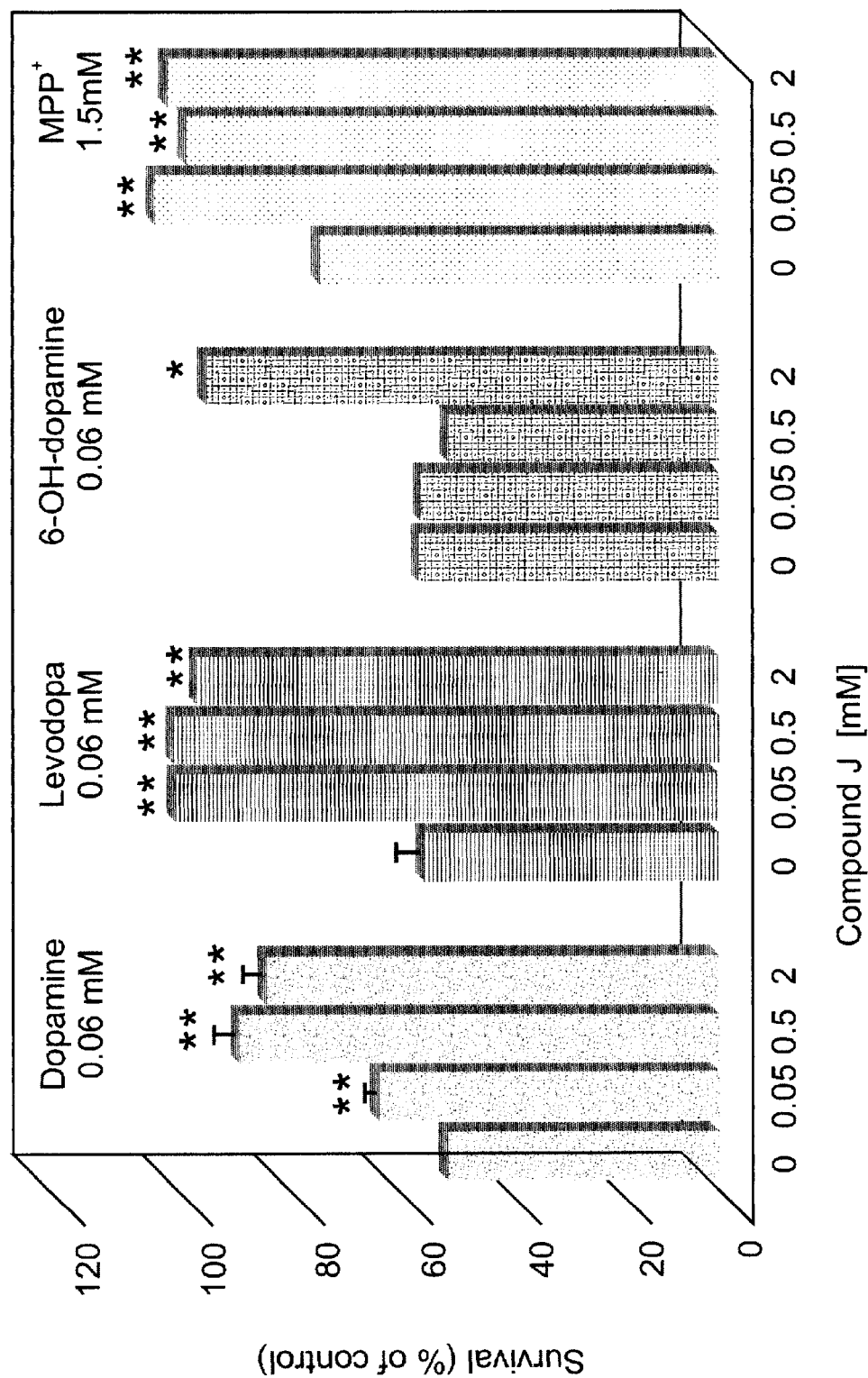
FIG. 4 demonstrates that Compound J at as low as 0.1 mM protect NB cells against the toxicity (>50%) of DA, L-dopa (levodopa), 6-OHDA (0.1–0.25 mM) and MPP$^+$ (0.5–2 mM). Cell survival was monitored by the neutral red assays.
Figure 5A:
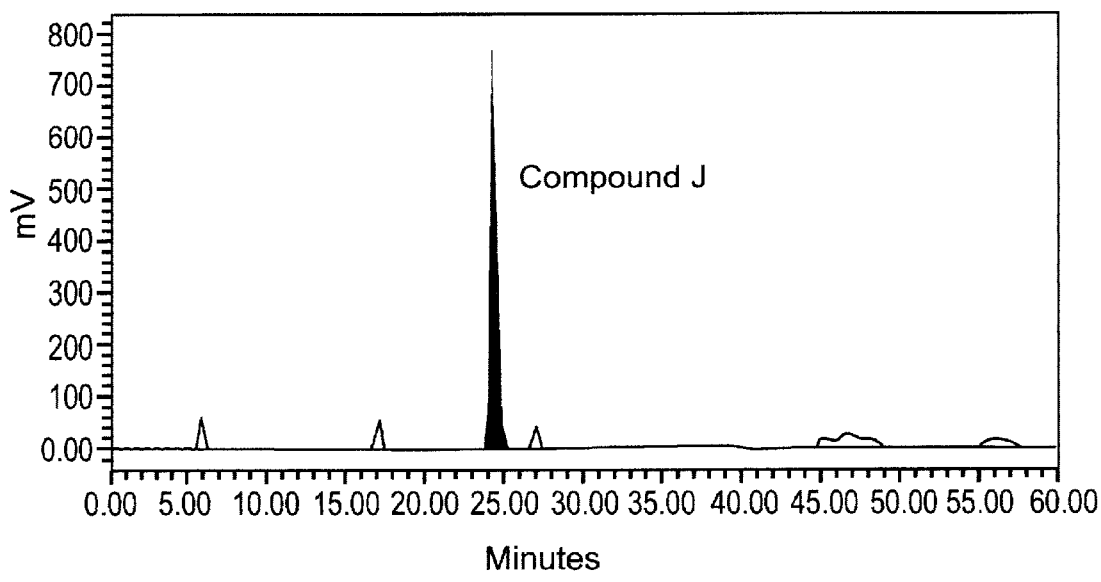
FIG. 5a shows HPLC profile of purified compound J.
Figure 5B:
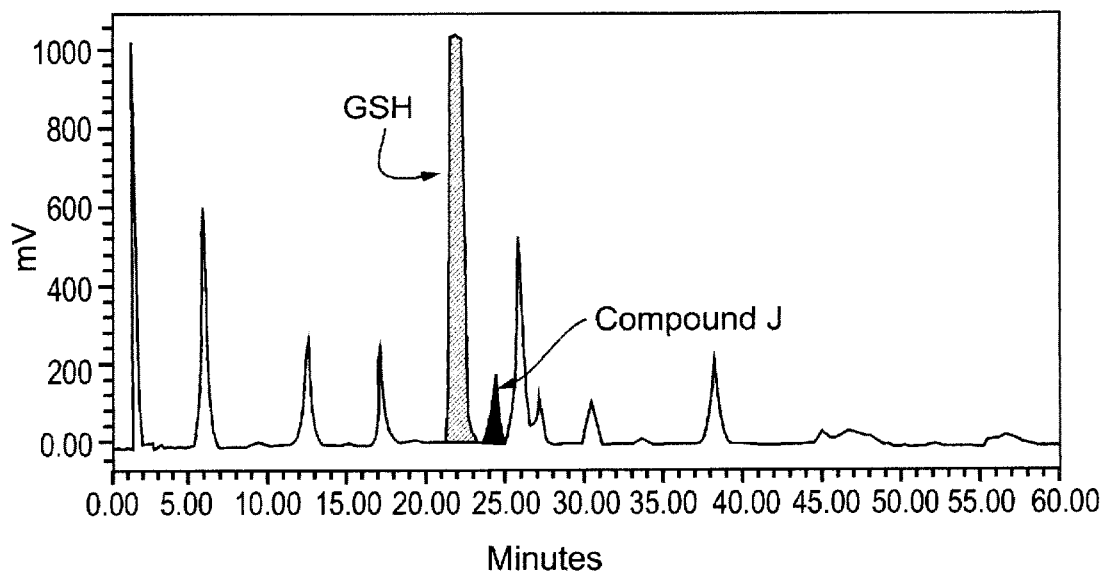
FIG. 5b shows HPLC profile of a brain extract of a mouse 15 minutes following IP injection of compound J.
Figure 6:
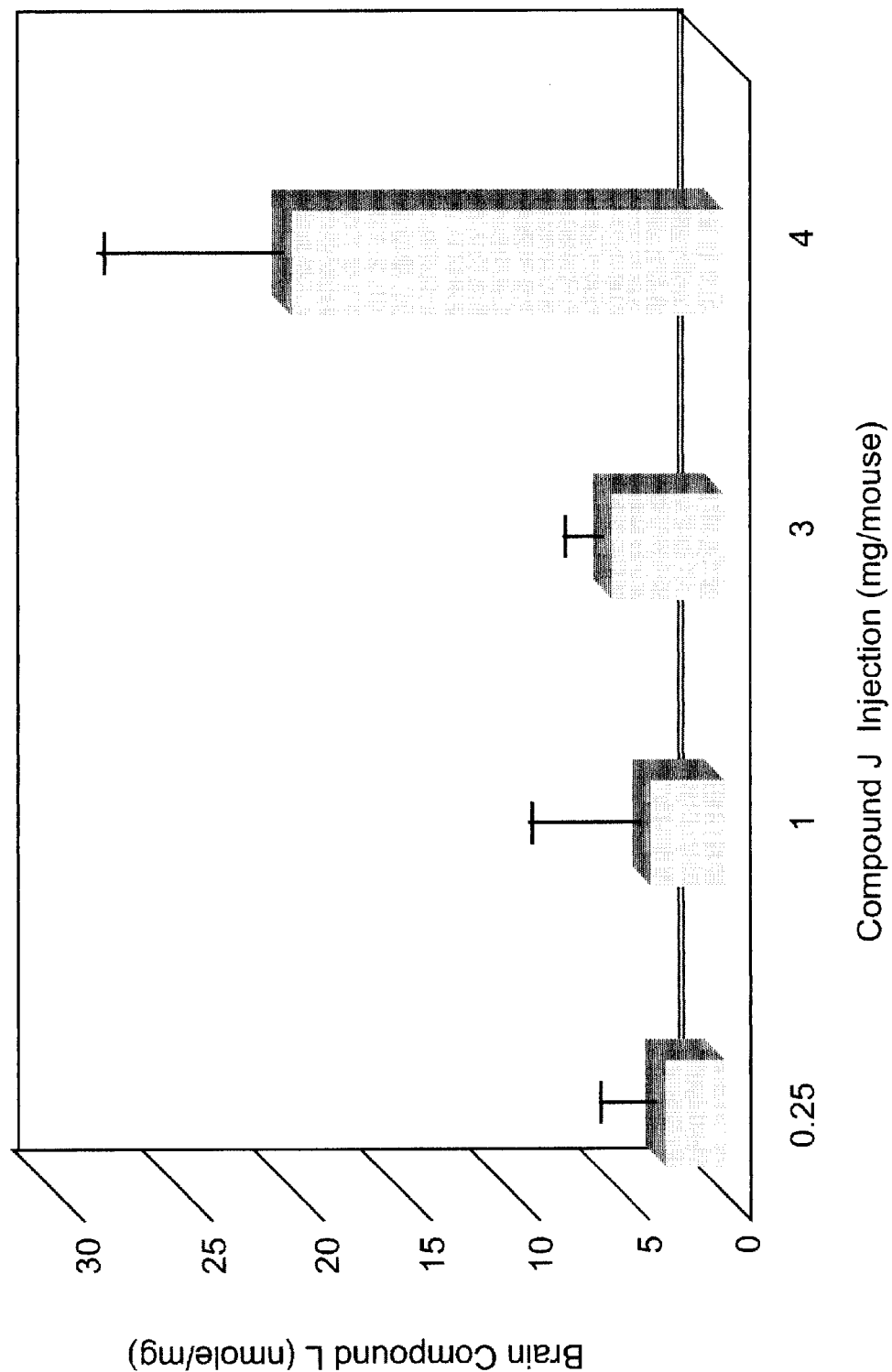
FIG. 6 shows the concentration of compound J in brain extracts of mice 15 minutes following IP injection of compound J at the amounts indicated.

The results are shown in FIGS. 4–6.

Increasing concentrations of compound J were added to NB cells compound J at 0.1 mM was found to protect the cells against the toxicity (>50%) of DA, L-dopa (levodopa), 6-OHDA (0.1–0.25 mM) and MPP$^+$ (0.5–2 mM). Cell survival was increased up to 95% in 0.3 mM compound J as indicated by neutral red assays (FIG. 4).

Increasing amounts of compound J were injected IP and 15 min later, mice were perfused with saline and compound J levels in the brain extracts were determined by HPLC chromatography (FIG. 5b), as compared to a control, pure, uninjected compound J (FIG. 5a).

IP injection of increasing concentrations (0.25–4 mg) of compound J showed a concentration-dependent increase of compound J in the brain (FIG. 6).

As shown in FIG. 5b, GSH levels were also increased in parallel to compound J presence showing up to 46% increase over untreated animals.

These data indicate that the newly synthesized thiol-substance, compound J effectively protects cells grown in tissue culture from oxidative stress. It crosses the BBB as shown by the combined fluorescent labeling and HPLC chromatography. Furthermore, it increases endogenous GSH levels in mice brain after IP injection.

Example 11

Animal Models for Focal and Global Brain Ischemia and Hypoxia

Examples 1–10 described hereinabove fully demonstrate the reduction to practice of the present invention. Not withstanding from the above, the following paragraphs describe some experimental procedures which may find use while preparing for clinical trials aimed at authorizing the use of the antioxidants described herein for use as medicaments in cases of brain ischemia.

Several animal models which are commonly used to determine focal and global ischemia, and brain hypoxia can be used to show the benefits of antioxidant compounds described herein. These animal models display selective biochemical parameters and clinical symptoms that can readily be monitored. These models provide a reliable and rapid estimation for both, progression of the diseases and recovery by putative neuroprotectors.

Each of the following test systems represents an aspect of neurotoxicity, which may be amenable to intervention by pharmaceutical agents that reduce brain oxidative stress. Using these systems, survival, clinical appearance and biochemical markers for free-radical production and ROS-induced damage in brain tissues can be monitored to further study the most effective dosage, time of administration and repetition rate.

Temporary global ischemia: Temporary blockade of blood supply to the gerbil brain is achieved by surgical ligation of the two major arteries (common carotids) at the neck. This procedure results in transient global forebrain ischemia and temporary global ischemia. This situation promotes a delayed, selective degeneration of neurons in the hippocampus, a brain structure essential for memory formation. The ability of various compounds to prevent hippocampal cell loss while the attendant memory deficits is considered a measure of their potency as neuroprotectants in ischemic conditions. Therefore, this assay is suitable for determining the potential protective properties of the antioxidants described herein.

Thus, the antioxidant compounds described herein can be tested for their ability to prevent neurological damage in gerbils, following bilateral common carotid artery ligation. To this end Mongolian gerbils (male), 60–70 grams in weight, can be used. Common carotid arteries (CCA) will be isolated and a silk suture will be loosely looped around them. The tips of each loop will be tied together, and the suture material will be buried beside the trachea. The ventral neck incision will then be sutured. In the following day, the animals will be lightly anaesthetized with ether, the neck skin wounds will be opened and both CCA will be occluded for 10 minutes using small artery clips. The test compounds will be administrated I.V. via the femoral vein, e.g., just before induction of ischemia, and 1 minute, 10 minutes and 2 hours later. Three to five hours later, animals will be observed for their clinical appearance at intervals of 24 hours, for three days. Each tested animal will be given a neurological score as follows: Normal 0; Sleepy/lethargic 1; Hyperactive 2; Circling/Ptosis 3; Jumping 4; Tossing seizures/Ophistotonus 5; Tonic convulsions 6; Coma, weak pain response 7; Coma, no pain response 8; Death 9. Three days following the ischemic insult, brains will be perfusion-fixed and subject to pathological and biochemical assays, as is further described below. Statistical analysis (ANOVA) will be used to establish the statistical significance of the observed results.

Permanent focal stroke: In humans, thrombotic or embolic occlusion of the middle cerebral artery (MCA) is a common cause of ischemic hemispheric stroke. In animals, coagulation, permanent ligation or permanent placement of an occluding thread in this artery produce a permanent focal ischemia within the MCA supply territory. Transient ligation or occlusion results in transient focal stroke. Both, transient and permanent focal strokes result in varying degree of edema and infarction in affected brain regions. The ability of the antioxidant compounds described herein to reduce the volume of edema and infraction will be taken as a measure to their usefulness as anti-stroke agents. To this end, the neuroprotective effect of the antioxidant compounds described herein will be assessed in a permanent focal ischemia model using rats in which the middle cerebral artery is electrically coagulated. In this model, the primary damage is not, in all likelihood amenable to pharmacological intervention. However, the secondary damage in the penumbra and thus the total infracted volume can be reduced by neuroprotective measures. The right femoral artery and vein will be cannulated with PE-SO poly-ethylene catheters for monitoring arterial blood pressure gases, and for drug administration. The cranial vault and the right side of the skull will be exposed via longitudinal incision between the eye and the ear. The zygomatic arch will be removed. A burr hole (1.5 mm in diameter) for a temperature probe will be drilled above the right parietal lobe by means of a high-speed mini-drill under an operating microscope, and the proximal portion of the right MCA will be electrocoagulated and severed. The test compounds will be administrated just before induction of ischemia, and 1 minute, 10 minutes and 2 hours later (subject to possible changes). Three days following the ischemic insult, brains will be perfusion-fixed for pathological and biochemical examinations as is further described below. Statistical analysis (ANOVA) will be used to establish the statistical significance of the observed results.

Global ischemia in rats: The blood supply to the rat brain is provided via the two vertebral and two common carotid arteries. Transient occlusion of all four vessels results in global ischemia, as would occur during cardiac arrest in humans. Global ischemia results in neurological impairments, including short term memory deficits, and a selective loss of neurons in the CA1 field of the hippocampus. The ability of the antioxidant compounds described herein to reduce the neurological deficits and to increase neuronal survival in this model is considered indicative of their potential of preventing brain damage related to cardiac arrest.

The 4-vessel occlusion (4 VO) rat model is often used as an animal model for brain ischemia, because it is relatively easy to produce and is highly reproducible. The 4 VO model is a more severe model of ischemia as is compared to the gerbil model described above and is usually not responsive to treatment. Animals will undergo four-vessel occlusion by a two-stage operation. On the first day, the vertebral arteries will be occluded. To this end, a midline skin incision is performed above the spinal cord, behind the skull occipital bone. Muscles are separated and cut until tC1 vertebra is isolated. The alar foramina are located and the vertebral arteries are coagulated. Muscles and skin are closed in two layers. Latter on the same day, the common carotid arteries (CCA) are isolated through a central neck midline incision. A loose suture material is positioned around them and the skin is closed. On the next day, the CCA are occluded. The animals will be lightly anesthetized (ether), the skin will be opened and CCA will be closed for 20 minutes with arterial clips. Early loss of righting reflex is the principal criterion for assuring occurrence of severe forebrain ischemia in the 4 VO model in the rat. Therefore, animals not showing this sign will not be included in the study. Animals will be assigned at random to a treatment group on the day of CCA occlusion. The tested antioxidant compounds will be administrated I.V. just before induction of the ischemia, and 1 minute, 10 minutes and 2 hours later (subject to changes). Three days following the ischemic insult, brains will be perfusion-fixed for pathological and biochemical examinations as is further described hereinbelow. Statistical analysis (ANOVA) will be used to establish the statistical significance of the observed results.

Hypobaric anoxia in mice: Exposure of mice to hypobaric (200 mmHg) atmosphere reduces the amount of oxygen available for the animals and results in death within 1–2 minutes. Pretreatment with compounds that can counteract the effects of oxygen deprivation could prolong the survival time of mice subjected to this treatment. An increase in survival time by systemically administrating the antioxidant compounds described herein will indicate their efficiency at counteracting anoxic damage in vivo.

Thus, exposure of mice to a hypobaric atmosphere (200 mmHg) results in death within a few minutes in normal, untreated animals. Hypobaric anoxia will be used as a test system for screening the neuroprotective effects of the antioxidant compounds described herein. To this end, mice in groups of ten will be placed in a chamber pre-equilibrated at hypobaric atmosphere of 200 mm Hg (air is pumped out of the chamber via a vacuum pump). The mice will be observed until they stop breathing and that time point will be recorded for each animal. The antioxidants will be administered 15 minutes before introducing the animals into the chamber.

Example 12

Pathological and Biochemical Analysis

In all of the models described under Example 11 above, brain damage will be evaluated using light microscope-scanning and other pathological and biochemical parameters.

Histology: For histopathological evaluation the animals will be perfused with 10% formaldehyde, brains will be removed and stored for one week. Then, 5 µm sections from the affected area in each model, will be stained with H&E and cresyl violet for measurement of infarct size. Measurements of volume of the infarcts, edema, and the penumbra in the experimental groups will give a good estimation for the possible beneficial protective effects of the antioxidant compounds described herein.

Biochemistry: Ischemic damage is associated with a series of biochemical changes. Since most of these changes occur around the infarct area, brain tissue of model animals will be subjected of measurements of the ROS-induced alterations. Thus, Oxidized proteins will be quantified as protein carbonyls using anti 2,4-dinitrophenylhydrazine (DNP) antibodies. Protein glycation will be estimated using rabbit antiserum to carboxy-methyl lysine, which was identified as a major glycation product. The changes in the GSH/GSSG oxidation-reduction system will be evaluated by measuring cellular levels of GSH and GSSG. Several methods including commercial kits (GSH-400) and DTNB will be applied. The GSH/GSSG ratio is an important marker that provides a good estimation for the oxidative status of the examined brain cell. Production of free radicals will be assayed using 2,7-dichloro-fluoresceine-diacetate (DCF) that measures intracellular level of OH radicals.

Immunohistochemistry: Ischemic damage is associated with an increase in xanthine dehydrogenase, xanthin oxidase, and a decrease in glial fibrillary acidic protein (GFAP). Utilizing specific antibodies and immunohistochemistry methods, the levels of these enzymes will be compared among treated and untreated animals and/or between the two brain hemispheres.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

LIST OF REFERENCES IN ALPHABETICAL ORDER

1. Brown, D. R., Schmidt, B. & Kretzschmar, H. A. Role of microglia and host prion protein in neurotoxicity of a prion protein fragment. Nature 380, 345–347 (1996).
2. Bundy, G. L., Ayer, D. E., Banitt, L. S., Belonga, K. L., Mizsak, S. A., Palmer, J. R., Tustin, J. M., Chin, J. E., Hall, E. D., Linseman, K. L., et al. Synthesis of novel 2,4-diaminopyrrolo-[2,3-d]pyrimidines with antioxidant, neuroprotective, and anti asthma activity. J Med Chem. 38, 4161–3 (1995).
3. Cafe, C., Torri, C., Betorelli, L., Angeretti, N., Luccan E., Forloni, G., & Marzatico, F., Oxidative stress after acute and chronic application of b-amyloid fragment 25–35 in cortical cultures. Neuroscience Letts. 203, 61–65 (1996).
4. Craig. C. Transcend therapeutics takes flight against oxidative stress public. BioWorld Today. Aug. 27, 1996, pp.1–2.
5. Fahn S. & Cohen, G. The oxidant stress hypothesis in Parkinson's disease: evidence supporting it. Ann Neurol. 32, 804–812 (1992).
6. Gash., D. M., Zhang, Z., Ovadia, A., Cass, W. A., Simmermann, A. Y. L., Russell., D., Martin, D., Lapchak, P. A., Collins, F., Hoffer, B. J. & Gerhardt, G. A. Furecovery in parkinsonian monkeys treated with GDNF. Nature, 380 252–255 (1996).
7. Jenner, O. Oxidative damage in neurodengenerative disease. Lancet, 344, 796–798 (1994).
8. Levy, E. G., Anderson, M. E. and Meister A. On the synthesis and characterization of N-formylglutathione and N-acetylglutathione. Anal. Biochem., 214, 135–137 (1993).
9. Martinuo et al. Overexpression of BCL-2 in transgenic mice protects neurons from naturally occurring cell death and experimental ischemia. Neuron., 13, 1017–30 (1994).
10. Offen, D., Ziv, I., Srernin, H., Melamed, E. and Hochman, A. Prevention of dopamine-induced cell death by thiol-antioxidants: Possible implications for treatment of Parkinson's disease. Exptt. Neurol., 141, 32–39 (1996).
11. Olanow, C. W. A radical hypothesis for neurodegeneration. Trends. Neurol. Soc. 16, 439–444 (1993).
12. Olanow, C. W. Oxidation reactions in Parkinson's disease. Neurology 40, 32–37 (1990).
13. Sian, J., Dexter, D. T., Lees, A. J.,. Daniel, S., Jenner, P & Marsden, C. D. Glutathione-related enzymes in brain in Parkinson's disease. Ann. Neurol. 36, 356–361 (1994).
14. Spencer, J. P., Jenner, A., Aruoma, O. I., Evans, P. J. Kauer, H., Dexter, D. T., Jenner, P., Lees, A. J., Marsden, D. C. & Haliwell, B. Intense oxidative DNA damage promoted by L-DOPA and its metabolites. FEBS Letts. 353, 246–250 (1994).
15. Takagi et al., Overexpression of thioredoxin in transgenic mice attenuates focal ischemic brain damage. Proc. Natl. Acad. Sci. U. S.A. 96, 4131–4136 (1999).
16. The Parkinson Study Group. Effects of tocopherol and deprenyl on the progression of disability in early Parkinson's disease. N. Eng. J. Med. 328, 176–183 (1993).
17. Thomas, T., Thomas, G. M., McLendon, C., Sutton, T. & Mullan, M. β-Amyloid-mediated vasoactivity and vascular endothelial damage. Nature 380, 168–171 (1996).

What is claimed is:

1. A method of therapeutically or prophylactically treating an individual against ischemic brain injury, the method comprising administering to the individual a pharmaceutical composition said pharmaceutical composition including a pharmaceutically acceptable carrier and a therapeutically or prophylactically effective amount of an antioxidant compound, said antioxidant compound having:
   (a) a combination of molecular weight and membrane miscibility properties which permits said compound to cross the blood brain barrier of the individual;
   (b) a sulfhydril group providing antioxidation properties; and
   (c) a chemical property for permitting said compound or its intracellular derivative to accumulate within brain cells of the individual.

2. The method of claim 1, wherein said compound is selected from the group consisting of N-acetyl cysteine ethyl ester (compound A), β,β-dimethyl cysteine ethyl ester (compound B), N-acetyl-β,β-dimethyl cysteine (compound C), Glutathione ethyl ester (compound D), N-acetyl glutathione ethyl ester (compound E), N-acetyl glutathione (compound F), N-acetyl α-glutamyl ethyl ester cysteinyl glycyl ethyl ester (compound G) N-acetyl α-glutamyl ethyl ester cysteinyl glycyl (compound H), N-acetyl glutathione amide (compound I), N-acetyl cysteine amide (compound J), N-acetyl β,β dimethyl cysteine amide (compound K) and N-acetyl cysteine glycine amide.

3. The method of claim 2, wherein said administration is systemic.

4. The method of claim 1, wherein said ischemic brain injury is a result of a stroke or a head trauma.

5. The method of claim 1, wherein said pharmaceutically acceptable carrier is selected from the group consisting of a thickener, a carrier, a buffer, a diluent, a surface active agent and a preservative.

6. The method of claim 1, wherein said administration is systemic.

7. The method of claim 6, wherein said systemic administration is selected from the group consisting of topical administration, oral administration, administration by inhalation, and parenteral administration.

8. The method of claim 1, wherein said individual is a human being.

* * * * *